United States Patent
Petschke, Jr.

(10) Patent No.: US 10,052,787 B1
(45) Date of Patent: Aug. 21, 2018

(54) SPIRIT FLAVORED AND SCENTED WOODEN ARTICLES

(71) Applicant: Thomas A. Petschke, Jr., Crestwood, KY (US)

(72) Inventor: Thomas A. Petschke, Jr., Crestwood, KY (US)

( * ) Notice: Subject to any disclaimer, the term of this patent is extended or adjusted under 35 U.S.C. 154(b) by 395 days.

(21) Appl. No.: 14/734,579

(22) Filed: Jun. 9, 2015

Related U.S. Application Data

(60) Provisional application No. 62/009,566, filed on Jun. 9, 2014.

(51) Int. Cl.
| | |
|---|---|
| *B27K 3/00* | (2006.01) |
| *B27K 3/08* | (2006.01) |
| *A61C 15/02* | (2006.01) |
| *A47J 43/27* | (2006.01) |
| *A47J 37/04* | (2006.01) |
| *B27K 3/02* | (2006.01) |

(52) U.S. Cl.
CPC ............ *B27K 3/08* (2013.01); *A47J 37/049* (2013.01); *A47J 43/27* (2013.01); *A61C 15/02* (2013.01); *B27K 3/0278* (2013.01)

(58) Field of Classification Search
CPC .................................. B27K 3/00; B27K 3/08
See application file for complete search history.

(56) References Cited

U.S. PATENT DOCUMENTS

| | | | | |
|---|---|---|---|---|
| 6,898,824 B2 * | 5/2005 | Zaltron | ................ | A63C 11/221 135/66 |
| 2012/0088018 A1 * | 4/2012 | Lix | ........................... | B24C 1/04 426/422 |
| 2013/0233340 A1 * | 9/2013 | Sapan | .................... | A61C 15/02 132/321 |
| 2015/0197715 A1 * | 7/2015 | Peniche | ................ | C12G 3/065 426/124 |

FOREIGN PATENT DOCUMENTS

| | | | | |
|---|---|---|---|---|
| CA | 2275836 A1 * | 12/2000 | ............. | B27G 1/00 |
| DE | 19834247 A1 * | 2/2000 | ............. | A61C 15/02 |
| JP | 01144924 A * | 6/1989 | | |
| JP | 2008220294 A * | 9/2008 | | |
| KR | 20110011302 A1 * | 2/2011 | | |
| WO | WO-9749795 A1 * | 12/1997 | ............. | C12G 3/065 |

OTHER PUBLICATIONS

Daneson. Single Malt No. 16. http://www.daneson.com available only 2013. Retrieved Oct. 12, 2017.*

Daneson. Single Malt No. 16. http://www.daneson.com available only 2013. Retrieved Oct. 12, 2017. (Year: 2013).*

(Continued)

*Primary Examiner* — David P Turocy

(74) *Attorney, Agent, or Firm* — MacMillan, Sobanski & Todd, LLC

(57) ABSTRACT

Wooden articles such as toothpicks, stir sticks, skewers and chopsticks made from substrate wood that has been impregnated with spirit liquid or vapor. The substrate may come from spirit producing barrels or from other wood involved in the spirit making process.

11 Claims, 10 Drawing Sheets

(56) References Cited

OTHER PUBLICATIONS

Spoons and Pulls, Oak Wine Barrell Staves. http://lumberjocks.com/projects/72453, Available 2012. Retrieved Nov. 22, 2017 (Year: 2012).*

Machine Translation of KR20110011302A1, retrieved Nov. 22, 2017. (Year: 2017).*

Shannon M. Nass. For a unique flavor, this time try smoking venison. Pittsburgh Post-Gazette. Dec. 4, 2011, retrieved online Nov. 27, 2017 (Year: 2011).*

Daneson, http://daneson.com/products/bourbon, Daneson Bourbon N° 22 Toothpicks, pp. 1-2 and Daneson Worthy & Fulsome Toothpicks, p. 1, dated Aug. 13, 2015.

* cited by examiner

SPIRIT FLAVORED AND SCENTED WOODEN ARTICLES

CROSS-REFERENCE TO RELATED APPLICATION

This application claims the benefit of U.S. Provisional Application No. 62/009,566, filed Jun. 9, 2014, the disclosure of which is incorporated herein by reference.

FIELD OF THE INVENTION

The present invention relates generally to wooden articles which contact food, drink, a user's mouth and more particularly to spirit flavored or scented articles.

BACKGROUND OF THE INVENTION

Wooden articles such as toothpicks, skewers, stir sticks, and chop sticks have been well known and used for centuries. The practice of flavoring toothpicks is known. The present invention enhances the benefits of flavored toothpicks and expands the use of this benefit to include skewers, stir sticks, chop sticks and other wooden articles.

Various methods exist to flavor wooden toothpicks after the substrate material has been formed into the shape of the toothpick. Typically, flavor is added to toothpicks only after the wood is processed into the shape of a toothpick. Previous methods of flavoring toothpicks have involved coating the toothpick, such as by dipping the toothpick into a flavor substance. These methods provide only a superficial, short-lived flavoring. The present invention uses wood that has been exposed to liquid spirits, vapors, or both prior to being formed into the shape of a toothpick, skewer, stir stick, chop stick, or other article.

In addition, current processes for manufacturing toothpicks, cooking implements such as skewers, drink implements such as stir sticks, and eating implements such as chop sticks, involve deforestation and the use of virgin wood. There exists a need for a more environmentally friendly way to manufacture these products.

SUMMARY OF THE INVENTION

The present invention is a wooden article impregnated with spirit residue. The article can be a toothpick, skewer, stir stick, chop stick, or other article. The articles are made by providing a wooden substrate, exposing the substrate to spirits, and then forming the article from the substrate. The spirits in this wood provide the user with the following advantages: pleasant aroma, nice taste, improved flexibility while maintaining strength. Food, liquid, or other substances that are held by the toothpick, skewer, stir stick, or chop stick can absorb the spirits, which provide additional flavor to the food or liquid.

Preferably, the wooden substrate is a stave from a used spirit aging barrel, but other methods of exposing the substrate to sprits may be used, such as injecting, soaking, pressurizing or vacuum infusing.

This invention utilizes the benefits of the substrate material being exposed to flavoring agents for extended periods of time and then manufacturing the toothpicks, skewers, stir sticks, and chop sticks from this substrate material.

Further features and advantages of the present invention will be apparent from the following detailed description.

DESCRIPTION OF PREFERRED EMBODIMENTS

Figure 1:
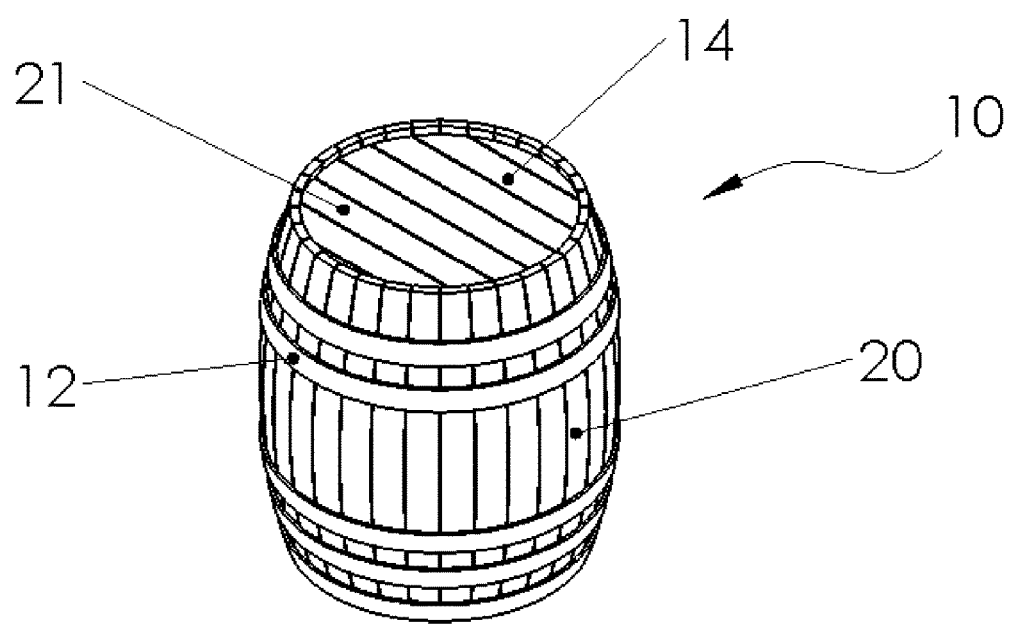
FIG. 1 is a perspective view of a wooden barrel used to age spirits.
Figure 2:
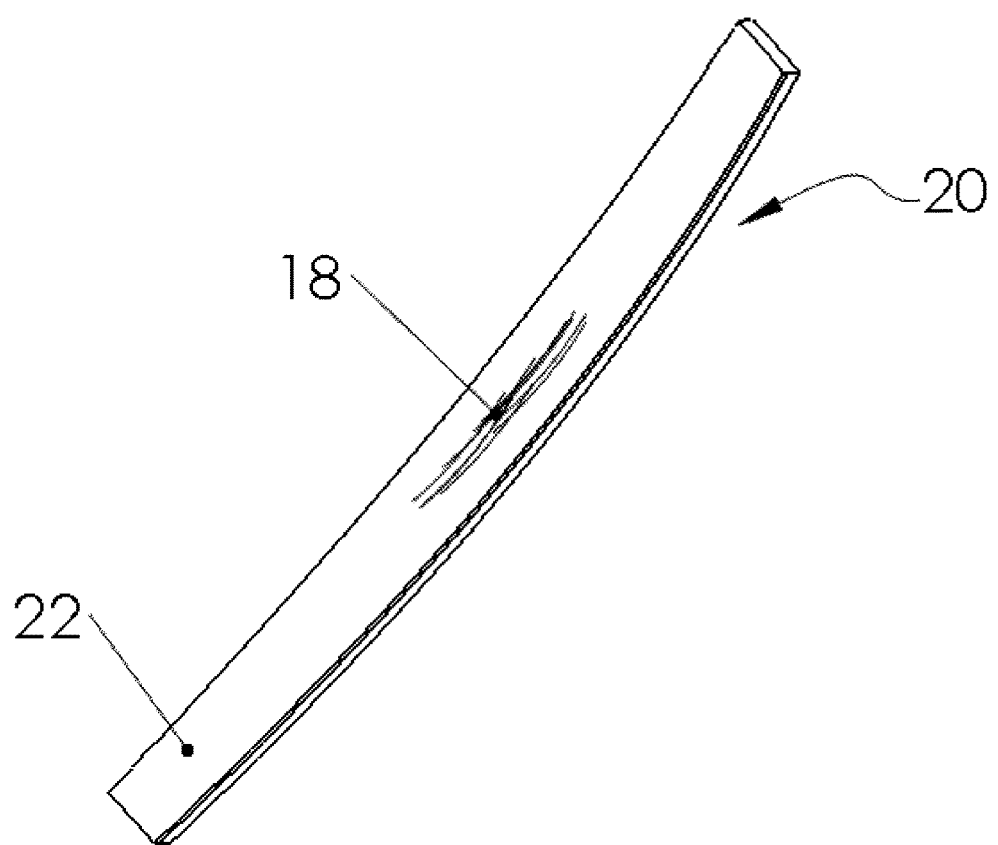
FIG. 2 is a perspective view of a stave used in the barrel of FIG. 1.

Referring to FIGS. 1 and 2, a typical 53-gallon American White Oak wooden barrel 10 has been used to hold spirits during the spirits aging process. The body of the barrel is formed from vertically extending curved wooden staves 20 secured by metal bands 12. The barrel cover 14, as well as the barrel bottom (not shown), are similarly formed from flat wooden staves 21, as is well known in the sprits industry. The staves 20, 21 provide a substrate for liquid and vapors to be absorbed from the spirits.

Figure 3:
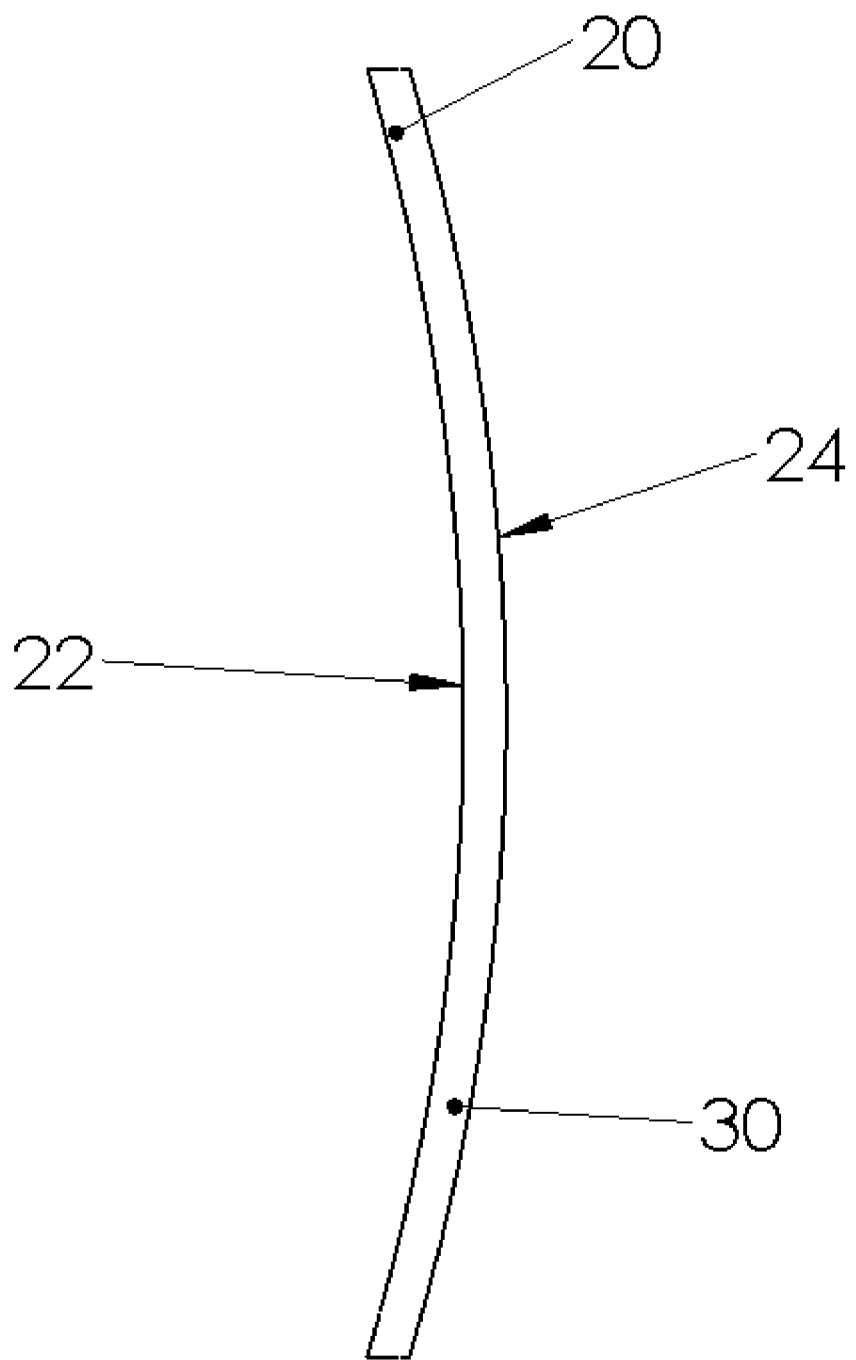
FIG. 3 is a side view of the stave of FIG. 2.
Figure 4:
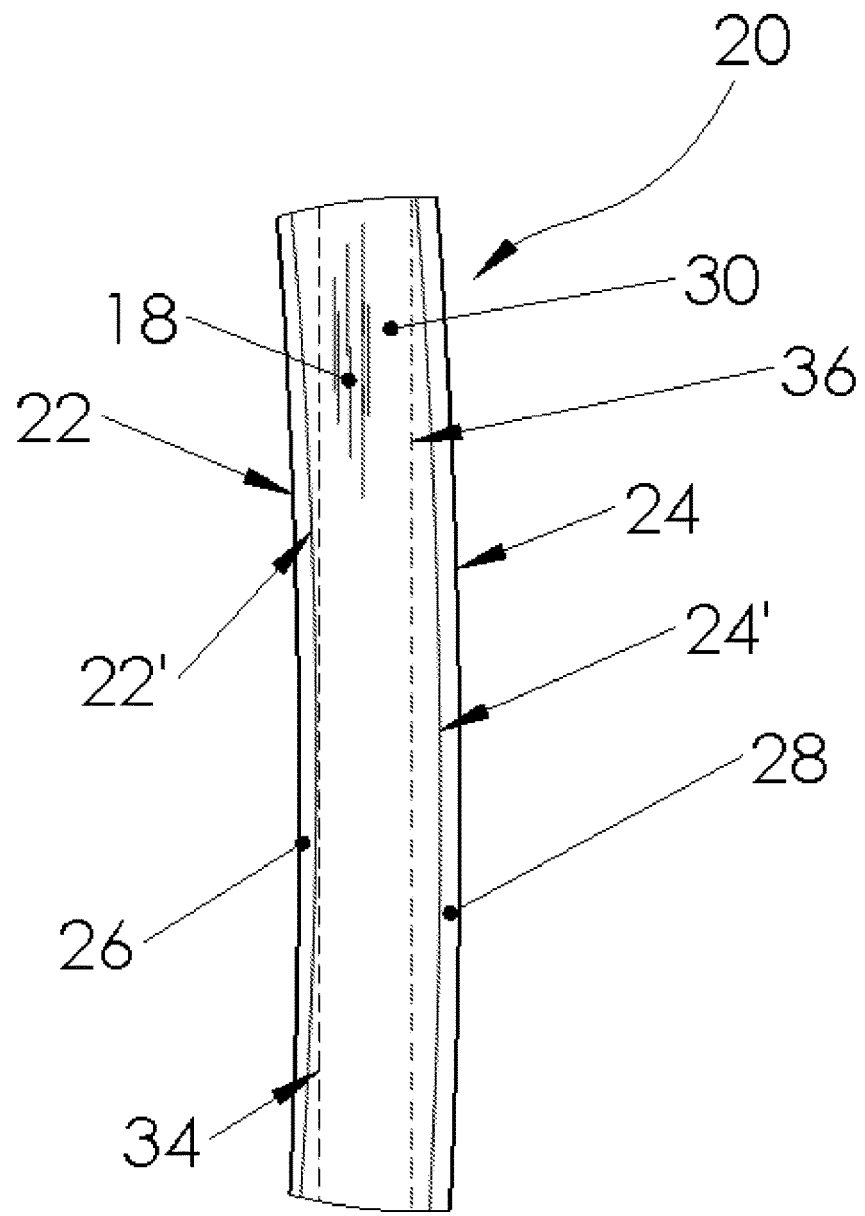
FIG. 4 is a longitudinal cross-sectional view of a portion of the stave of FIG. 3.

Referring to FIG. 3, while the spirits age, typically over several years, the inner side 22 of the wooden staves are exposed to the spirits, and the wooden substrate absorbs portions of the spirits. Referring also to FIG. 4, the wood grain 18 of barrel staves typically extend lengthwise relative to the length of the stave. The outer surfaces 24 of the barrel staves are rough and potentially dirty and the inside surfaces 22 are charred and "flaky". A thin layer 26 is removed from the inner surface 22, and a thin layer 28 is removed from the outer surface 24 to expose surfaces 22' and 24', the "heartwood" 30 from which the flavored and scented articles will be made. The heartwood of the stave will have more concentration of imbedded spirits at the inner side compared to the outer side, but the articles can be made from the entire stave after the thin layers 26, 28 are removed.

Staves 20 may be reduced in length for easier processing. FIG. 4 shows a portion of a stave 20 which has been cut in half, for example. The stave portion is flattened by running the inside surface 22 on a joiner (not shown), as is well known in the woodworking industry. Several passes, each removing about 1/16 inches of wood, may be required to achieve a flat inner surface 34 (shown in phantom in FIG. 4). A planer (not shown) may be used to similarly remover portions of the outer surface 24 to achieve a flat outer surface 36 (also shown in phantom). Elongated articles are more easily produced from the flattened stave portions.

Figure 5:
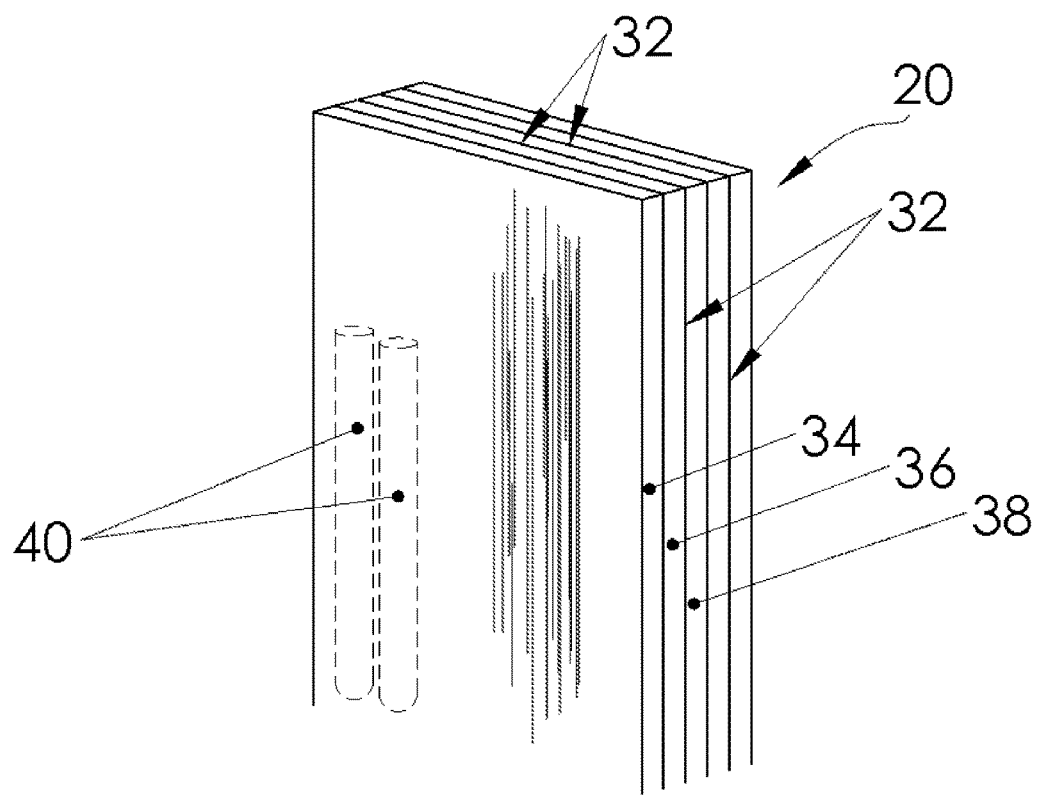
FIG. 5 is a plan view of the stave of FIG. 4.

FIG. 5 shows the stave 20 with cut lines 32 for producing thin stave boards 34, 36, 38, etc. The boards 34, 36, 38, etc. can have a thickness of about 0.1 to 0.25 inches, corresponding to the thickness of the articles 42 which are to be produced from the boards. Articles 42 can be made utilizing the entire depth of the stave 20, e.g. the entire heartwood, from the inner surface 22' to the outer surface 24'. The heartwood nearer the inner surface 22' may have slightly more spirit residue, and therefore a higher concentrations of flavor and scent, than the heartwood nearer the outer surface 24', as the amount of spirit residue will gradually decrease toward the outside surface 24'. The amount of residue may be tailored to each product, but flavor may also be balanced by post manufacturing processes. In addition, flavor and scent may be enhanced with post production processes as will be explained.

Referring to FIG. 5, cylindrical dowel cut lines 40 are shown in phantom may be produced from the stave boards 34, 36, etc. with equipment and processes well known in the woodworking industry. Dowels 40 can then be cut to length for producing wooden articles such as toothpicks, skewers, stir sticks, chopsticks, or other articles. Some waste is typical to the manufacturing process; some saw dust and wood shavings will be generated. The wood shavings, chips, etc. may be used for flavoring beverages such as beer and wine and non-alcoholic beverages such as tea and juices.

Figure 5A:
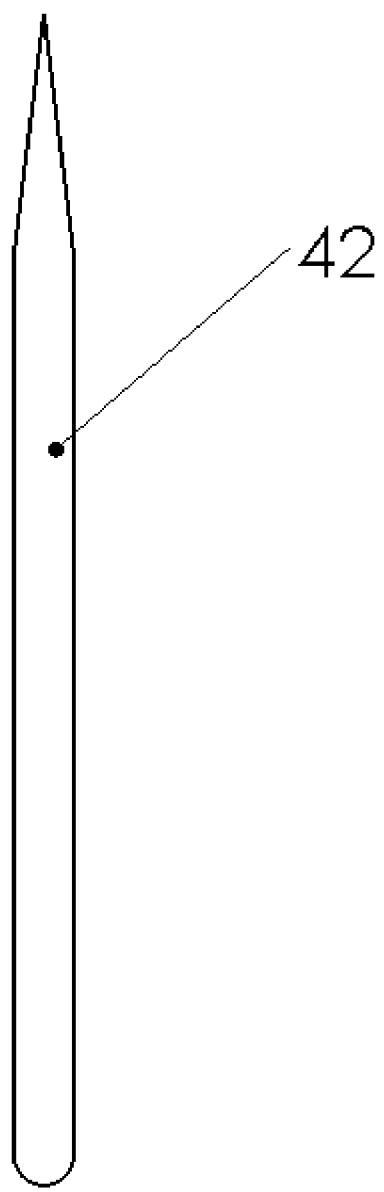
FIG. 5A is a schematic representation of a generic article produced from the stave of FIG. 5.

FIG. 5A illustrates an elongated article 42 which can be produced from a dowel 40 the stave 20 as shown. It is preferred that the wooden article 42 be produced along the wood grain 18 as shown, although other orientations are possible as well. The article 42 may be provided with pointed ends or other configurations.

Figure 5B:
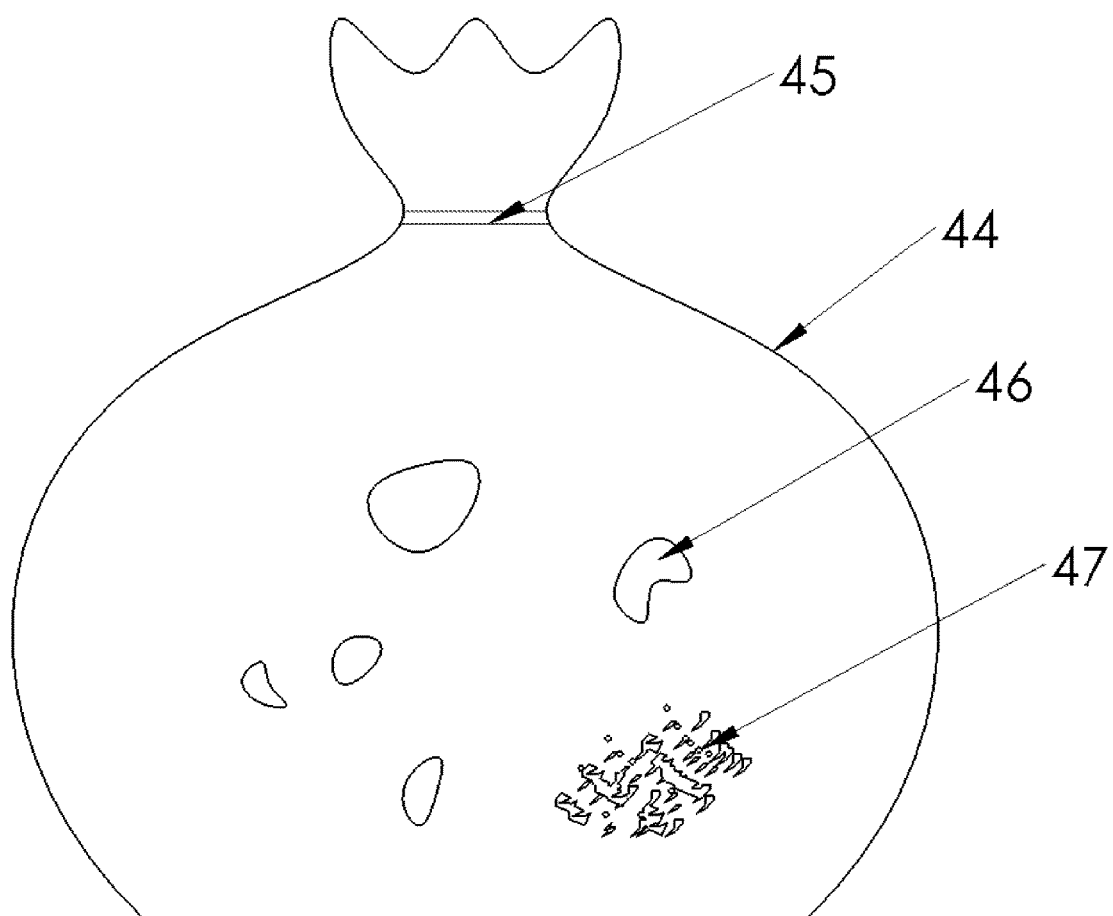
FIG. 5B is a schematic representation of a container of articles produced from the stave of FIG. 5.

FIG. 5B shows a permeable flavor pouch or bag 44 secured with a tie 45. The pouch contains wooden chips 46 and fragments (or sawdust) 47 produced from the stave 20. The chips or fragments may be produced intentionally or may be the remnants from producing other articles such as 42. The chips and/or fragments may be used to add flavor to beverages such as beer, wine, and juices or may be used to create a tea. The flavor pouch 44 is optional, as the chips and fragment may be added to any liquid directly or with other types of holding devices. Also, the chips and/or fragment can be used to add flavor to food by use in a smoker or on a grill.

Typical articles 42 that can be produced from typical barrel staves include toothpicks (approximately 2.5 inches long and about 0.1 inch diameter if round or on a side if square or rectangular, pointed on one or both ends), skewers (about 10-12 inches long and about 0.125 inches in diameter if round or on a side if square or rectangular, pointed on one or both ends), stir sticks (about 4-6 inches long and about 0.125 inches in diameter if round or on a side if square or rectangular, optionally round or squared on one or both ends and can be hollow to be used as a straw), and chop sticks (about 7-10 inches long with constant or varied thickness). The manufacturing equipment used to process the toothpicks, skewers, stir sticks, chop sticks and other articles is typical wood working equipment along with custom fabricated machines.

Figure 6:
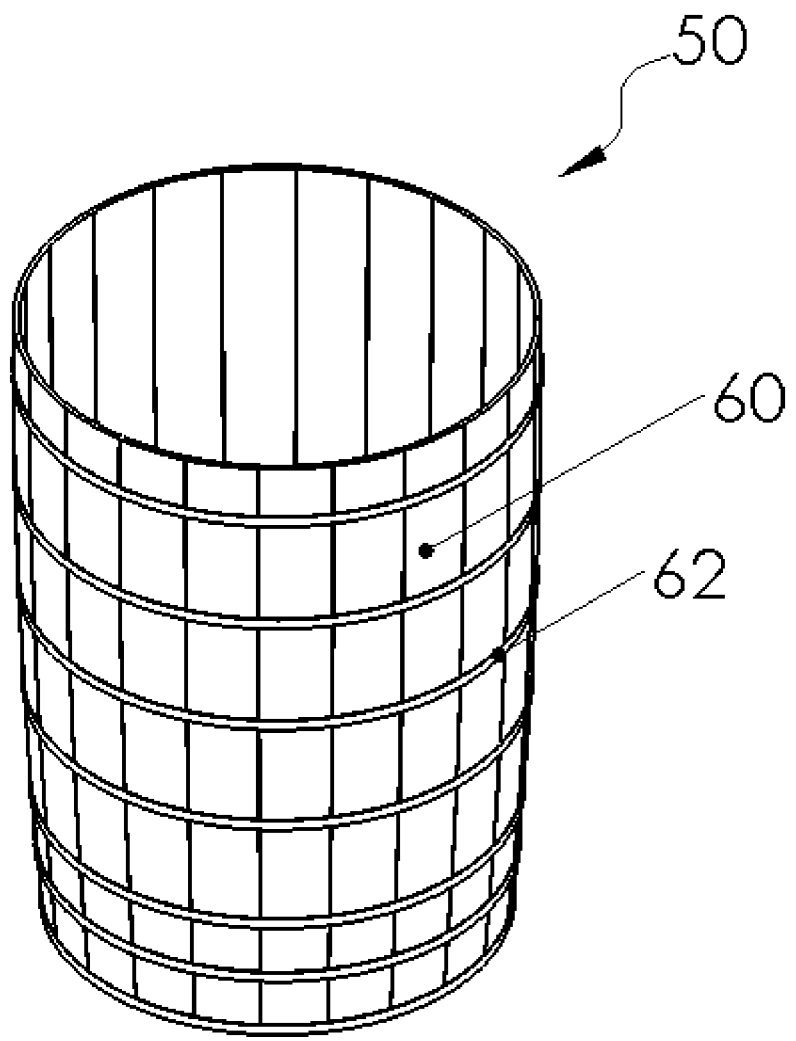
FIG. 6 is a view of a wooden mash tub.

FIG. 6 shows a typical wooden mash tub 50 used to hold mash during the sprits distilling process. The body of the tub is formed from vertically extending wooden staves 60 secured by metal bands 62. The staves 60 are similar to the barrel staves 20. The tub 50 is generally uncovered but has a bottom that is similarly formed from flat wooden staves as is well known in the sprits industry. Similar to staves 20, the staves 60 provide a substrate for liquid and vapors to be absorbed from the mash. As used in this application, "spirits" includes "mash."

Method of Making

The preferred method of producing wooden articles 42 with impregnated spirits liquid or vapors utilizes wooden barrel staves, preferably the wood staves from barrels involved in the aging or processing of spirits, such as bourbon, scotch, whisky, wine, liqueurs, cordials, tequila, rum, beer, etc. Articles made in accordance with the present invention contain some amount of the spirits absorbed from spirit liquid or vapors. Beginning the flavoring process with the substrate material allows for a longer lasting and more uniform saturation of the flavor and scent into the end articles as the spirits evaporate out of the wood.

The preferred process begins with filling a wooden barrel with spirits and aging the spirits in a typical fashion. American White Oak is preferred because the bourbon industry typically uses this wood, and because virgin barrels are required for spirits to qualify legally as "bourbon." Toothpick, skewer, stir stick, and chop stick manufacturers have been criticized for utilizing wasteful wood harvesting practices. The present invention helps reduce these wasteful practices. This invention uses recycled wood involved in the manufacture and aging process of spirits. This method is environmentally friendly and reduces deforestation and the use of virgin material.

The present invention also may be applicable to other types of wood. Spirits making barrels are commonly made from various other types of wood, including Red Oak, Spruce, Pine, Pine-Albion, Chestnut, Acacia, Fruitwoods, Chestnut Botti, Hickory, Beech, Maple, Cherry, and Birch. The traditional material used to produce toothpicks and stir sticks is birch, while skewers may be made from bamboo. Chop sticks are often made from Aspen, Chestnut, persimmon, pine, cedar, cherry, sandalwood, and *paulownia*. These woods can be used for the alternative processes if barrels are not available.

Figure 7:
FIG. 7 is a cross-sectional view of a wooden barrel containing wooden materials.

While the use of wood barrel or tub staves is preferred, alternative methods are also practical. For example, wood substrate material can be placed into a barrel during the spirits aging process, or into any suitable vessel containing spirits, with the substrate materials being totally or partially submerged in the spirits. FIG. 7 shows a spirits barrel 68 similar to barrel 10 for aging spirits. Barrel 68 contains wooden boards or planks 70 submerged in the spirits. These planks 70 can be used as the substrate to form flavored and scented wooden articles 42 in a manner similar to that used with the wooden staves 20.

Figure 8:
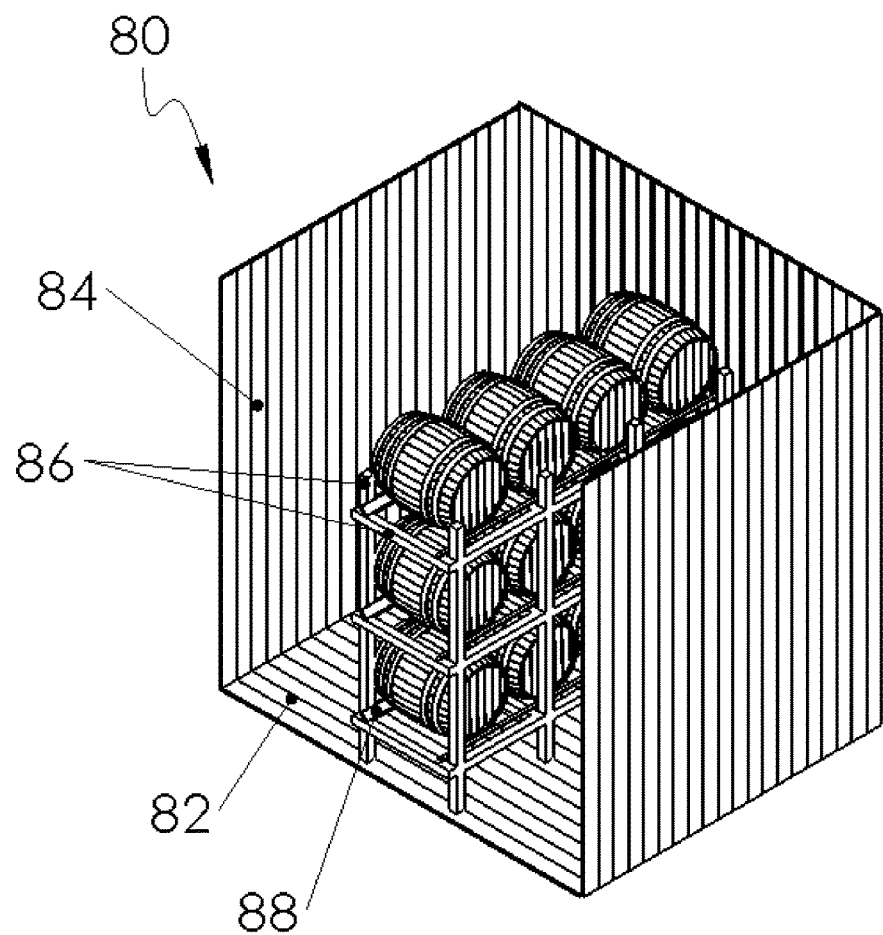
FIG. 8 is a schematic view of a wooden barrel storage unit.

FIG. 8 a wooden spirits barrel storage unit 80 including-wooden floors 82, wooden walls 84, and wooden racks 86, and wooden barrel supports 88. All of these wooden components of the unit are exposed to some level of spirit vapors, and all may be used to produce scented or flavored articles 42. The present invention is applicable to any wood involved in the production of spirits.

Other methods maybe used to impregnate spirit flavor or scent into wooden substrates. For example, spirits may be injected into the substrate, with the substrate optionally hollowed out before injecting, vacuum infusing sprits into a wooden substrate, and providing pressure to accelerate the spirits infusing process. These operations can be performed using vacuum chambers or similar equipment.

After the articles 42 are formed from the substrate, post formation treatment can include sanding and/or polishing to create a smooth exterior surface. The articles may also be soaked in spirits to add sprits into the articles. The articles may be soaked in other flavoring agents and/or sealed with candy, chocolate, or other edible product coatings to hold the spirits in the wood. The sealer may be an edible topcoat applied to all or part of the article to hold in the spirits. The sealer, topcoat or other coating may include a flavoring, candy (such as chocolate) to add flavor to the article.

The added flavor and aroma to all of these products provides many benefits, such as overcoming of oral fixations such as smoking and over-eating, adding flavor to food and beverages that come into contact with these products, and a providing a pleasant aroma for the user.

The descriptions of specific embodiments of the invention herein are intended to be illustrative and not restrictive. The invention may be practiced otherwise than as specifically explained and illustrated without departing from its spirit or scope as defined by the appended claims.

What is claimed is:

1. A method of making a toothpick comprising the sequential steps of:
   providing a barrel having staves,
   exposing a barrel stave to spirits, and
   forming the toothpick having a width of about 0.1 inches from the barrel stave after the barrel stave has been exposed to the spirits.

2. The method of claim 1 further comprising the step of removing a layer of the barrel stave surface to expose heartwood prior to forming the toothpick.

3. The method of claim 1 wherein the barrel stave is elongate and wherein the grain of the barrel stave is substantially aligned with the length of the barrel stave, and wherein the toothpick is elongate, and wherein the grain is substantially aligned with the length of the toothpick.

4. The method of claim 1 wherein the barrel stave is oak.

5. The method of claim 4 wherein the barrel stave is American White oak.

6. The method of claim 1 further comprising the step of applying a coating to the toothpick after the toothpick is formed.

7. The method of claim 1 wherein the toothpick has a length of about 2.5 inches.

8. The method of claim 7 wherein the toothpick has a width of about 0.10 inches.

9. The method of claim 1 wherein the stave is provided with a flat surface prior to forming the toothpick.

10. The method of claim 9 wherein the stave is cut into a thin board having a thickness of 0.1 to 0.25 inches prior to forming the toothpick.

11. A method of making a toothpick comprising the sequential steps of:
    providing a barrel having staves,
    exposing a barrel stave to spirits,
    forming the toothpick having a length of about 2.5 inches from the barrel stave after the barrel stave has been exposed to the spirits, and
    wherein the stave is cut into a thin board having a thickness of 0.1 to 0.25 inches prior to forming the toothpick.

* * * * *